US00PP11335P

United States Patent [19]

Dümmen

[11] Patent Number: Plant 11,335

[45] Date of Patent: Apr. 11, 2000

[54] POINSETTIA PLANT NAMED 'DUEDELUXE'

[75] Inventor: Marga Dümmen, Rheinberg, Germany

[73] Assignee: Dummen Jungpflanzenkulturen, Rheinberg, Germany

[21] Appl. No.: 09/105,362

[22] Filed: Jun. 26, 1998

[51] Int. Cl.[7] ..... A01H 5/00

[52] U.S. Cl. ..... Plt./307

[58] Field of Search ..... Plt./307

[56] References Cited

U.S. PATENT DOCUMENTS

P.P. 7,874 5/1992 Fruehwirth ..... Plt./307

P.P. 8,250 6/1993 Trees ..... Plt./307

P.P. 9,632 8/1996 Trees ..... Plt./307

P.P. 9,854 4/1997 Dümmen ..... Plt./307

*Primary Examiner*—Howard J. Locker

*Assistant Examiner*—Kent L. Bell

*Attorney, Agent, or Firm*—C. A. Whealy

[57] ABSTRACT

A new and distinct variety of Poinsettia plant named 'Duedeluxe', characterized by its red flower bracts; flat flower bracts horizontal or angled slightly upright with respect to stem axis; very dark green foliage; freely branching plant habit; and excellent postproduction longevity.

1 Drawing Sheet

BACKGROUND OF THE INVENTION

The present invention relates to a new and distinct cultivar of Poinsettia plant, botanically known as *Euphorbia pulcherrima* Willd., and hereinafter referred to by the name 'Duedeluxe'. The new Poinsettia is a product of a planned breeding program conducted by the Inventor in Rheinberg, Germany. The objective of the breeding program was to develop new Poinsettias that are freely branching; flower early; have desirable flower bract and leaf color; and have excellent postproduction longevity. The new Poinsettia originated from a cross made by the Inventor of the proprietary Poinsettia selection identified as code number E-2 as the male or pollen parent with a proprietary Poinsettia selection identified as code number M-128 as the female or seed parent. 'Duedeluxe' was discovered and selected in 1995 by the Inventor as a single flowering plant within the progeny of the stated cross in a controlled environment in Rheinberg, Germany. Asexual reproduction of the new Poinsettia by terminal cuttings taken at Rheinberg, Germany, has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Duedeluxe'. These characteristics in combination distinguish 'Duedeluxe' as a new and distinct variety:

1. Red flower bracts.
2. Flat flower bracts horizontal or angled slightly upright with respect to stem axis.
3. Very dark green foliage.
4. Freely branching plant habit.
5. Excellent postproduction longevity.

In side-by-side comparisons conducted by the Inventor in Rheinberg, Germany, plants of the new Poinsettia are more freely branching, and have smaller and more intense red bracts than plants of the male parent, selection number E-2. Compared to plants of the female parent, selection M-128, plants of the new Poinsettia have darker green, more deeply lobed foliage and more intense and brighter red bract color.

Plants of the new Poinsettia can be compared to plants of the Poinsettia cultivar 'Duewi' (disclosed in U.S. Plant Pat. application Ser. No. 09/105,363). However, in side-by-side comparisons conducted by the Inventor in Rheinberg, Germany, plants of the new Poinsettia flower slightly earlier, bracts are more upright, and leaves tend to be more deeply lobed than bracts and leaves of plants of the cultivar 'Duewi'.

Plants of the new Poinsettia can be compared to plants of the Poinsettia cultivar '490' (disclosed in U.S. Plant Pat. No. 7,825). However, in side-by-side comparisons conducted by the Inventor in Rheinberg, Germany, bracts of plants of the new Poinsettia are brighter red in color, smaller, and are held more upright than bracts of plants of the cultivar '490'. In addition, leaves of plants of the new Poinsettia are more deeply lobed than leaves of plants of the cultivar '490'.

BRIEF DESCRIPTION OF THE PHOTOGRAPH

The accompanying colored photograph illustrates the overall appearance of the new Poinsettia, showing the colors as true as it is reasonably possible to obtain in a colored reproduction of this type. The photograph comprises a top perspective view of a typical plant of 'Duedeluxe' that was pinched and grown in a 15-cm container. Bract and leaf colors in the photograph may appear lighter than the actual colors due to light reflectance.

DETAILED BOTANICAL DESCRIPTION

Plants of the new Poinsettia have not been observed under all possible environmental conditions. The phenotype may vary somewhat with variations in environment such as temperature, daylength and light intensity, without, however, any variance in genotype. The following observations and measurements describe plants grown in Rheinberg, Germany, under commercial practice in a glass-covered greenhouse with day temperatures about 22° C., night temperatures about 18° C. and light levels about 30,000 to 40,000 lux. Plants were grown in 15-cm pots, pinched one time, and flowered under long nyctoperiods. In the following description, color references are made to The Royal Horticultural Society Colour Chart except where general terms of ordinary dictionary significance are used.

Botanical classification: *Euphorbia pulcherrima* Willd. cultivar 'Duedeluxe'.

Parentage:

*Male, or pollen, parent.*—Proprietary selection of *Euphorbia pulcherrima* Willd. identified as code number E-2 .

*Female, or seed, parent.*—Proprietary selection of *Euphorbia pulcherrima* Willd. identified as code number M-128.

Propagation:

*Type cutting.*—Terminal cuttings.

*Time to initiate roots.*—Summer: About 10 days at 22° C. Winter: About 14 days at 22° C.

*Time to develop roots.*—Summer: About 21 days at 22° C. Winter: About 28 days at 22° C.

*Rooting habit.*—Thick, freely branching.

Plant description:

*Plant form.*—Inverted triangle, top of plant rounded.

*Growth habit.*—Freely branching and upright. Branching is enhanced by removing the shoot apex. Moderate growth rate and vigorous. Suitable for 10 to 16-cm containers.

*Plant height.*—About 23.5 cm.

*Crop time.*—From rooted cuttings to a flowering plant in a 15-cm container, about 11 weeks are required.

*Foliage description.*—Quantity of leaves: About 75 per flowering plant. Length: About 9.25 cm. Width: About 7.75 cm. Shape: Deltoid, palmatifid, lobed. Apex: Apiculate. Base: Acute. Margin: Entire. Texture: Velvety, glabrous. Color: Young foliage, upper surface: 131A. Young foliage, lower surface: 132B. Mature foliage, upper surface: 131A. Mature foliage, lower surface: 132B. Venation, upper surface: 135B. Venation, lower surface: 135C. Petiole: Length: About 5 cm. Color: 59A.

Inflorescence description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under long nyctoperiod conditions.

*Time to flower.*—About eight weeks under long nyctoperiod conditions.

*Quantity of inflorescences.*—One per lateral branch, usually about seven per plant.

*Inflorescence size.*—Diameter: About 22.5 cm. Height (depth): About 4 cm.

*Flower bracts.*—Orientation: Horizontal to angled slightly upright. Quantity of flower bracts per inflorescence: About 12 per inflorescence. Length: About 9 cm. Width: About 6.5 cm. Shape: Roughly ovate, occasionally lobed. Apex: Apiculate. Margin: Entire. Base: Acute to obtuse. Texture: Smooth, satiny. Color: Mature, upper surface: 46A. Mature, lower surface: 47A. After senescence, upper surface: 53A.

*Cyathia.*—Quantity: Usually about nine per corymb. Diameter of cyathia cluster: About 2.75 cm. Length: About 1.2 cm. Width: About 5.5 mm. Color: Immature: 140A. Mature: 140B. Peduncle: Length: About 1.9 cm. Aspect: Erect. Color: 53A. Stamens: Stamen number: About nine per cyathium. Anther size: About 1 mm. Anther shape: Rounded. Anther color: 59B. Pollen color: 8A. Pistils: Pistil number: Typically one per cyathium. Stigma shape: Trilobate. Stigma color: 59B. Style length: About 2 mm. Style color: 59B. Ovary number: Three. Nectaries: Usually one and sometimes two per cyathium.

Disease resistance: No fungal, bacterial nor viral problems observed on plants grown under commercial conditions.

Postproduction longevity: Generally plants maintain good substance and bract color for about five to six weeks under interior conditions.

It is claimed:

1. A new and distinct variety of Poinsettia plant named 'Duedeluxe', as illustrated and described.

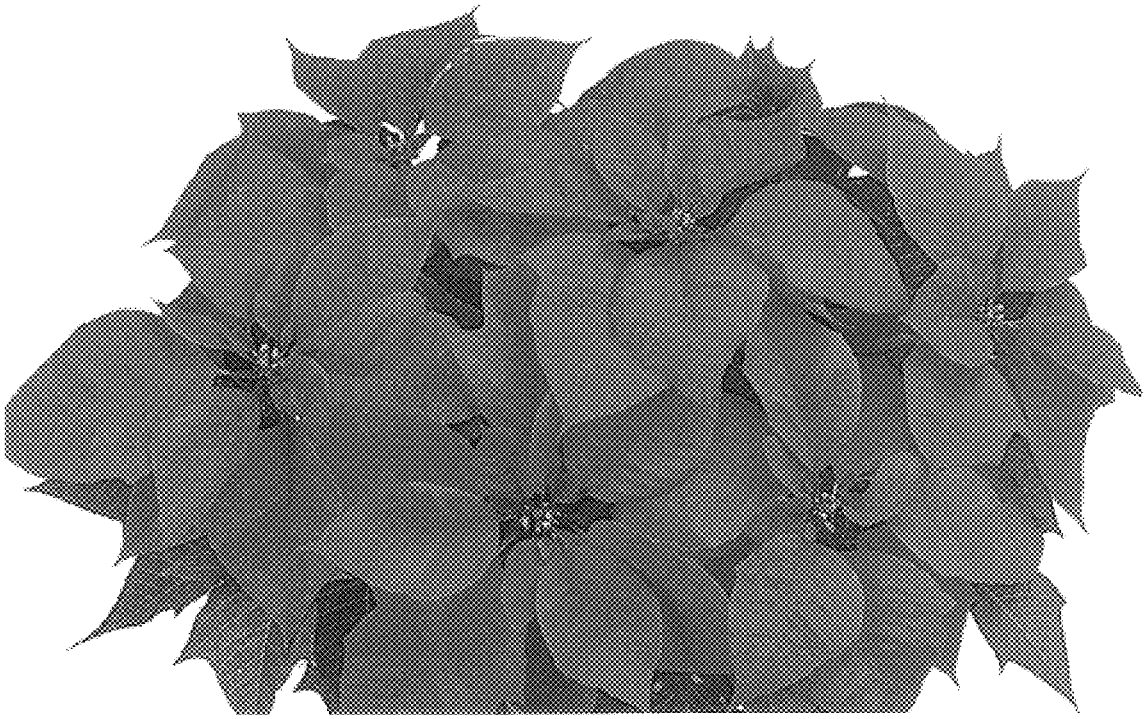

* * * * *